(12) United States Patent
Xu

(10) Patent No.: US 9,421,075 B2
(45) Date of Patent: Aug. 23, 2016

(54) INDEPENDENT LOW FRICTION BRACKET

(75) Inventor: Tianmin Xu, Beijing (CN)

(73) Assignee: Tianmin Xu, Beijing (CN)

( * ) Notice: Subject to any disclaimer, the term of this patent is extended or adjusted under 35 U.S.C. 154(b) by 0 days.

(21) Appl. No.: 13/818,073

(22) PCT Filed: Jan. 10, 2012

(86) PCT No.: PCT/CN2012/000038
§ 371 (c)(1),
(2), (4) Date: Feb. 20, 2013

(87) PCT Pub. No.: WO2012/103775
PCT Pub. Date: Aug. 9, 2013

(65) Prior Publication Data
US 2013/0157215 A1 Jun. 20, 2013

(30) Foreign Application Priority Data

Feb. 1, 2011 (CN) .......................... 2011 1 0034375

(51) Int. Cl.
*A61C 7/28* (2006.01)
*A61C 7/16* (2006.01)
*A61C 7/20* (2006.01)

(52) U.S. Cl.
CPC ... *A61C 7/28* (2013.01); *A61C 7/16* (2013.01); *A61C 7/20* (2013.01)

(58) Field of Classification Search
CPC ............ A61C 7/12; A61C 7/14–7/145; A61C 7/148–7/18; A61C 7/22; A61C 7/28; A61C 7/30–7/306

USPC ................................ 433/8–10, 15, 18, 20, 24
See application file for complete search history.

(56) References Cited

U.S. PATENT DOCUMENTS 4,687,441 A * 8/1987 Klepacki ................ A61C 7/125
433/8
5,030,089 A 7/1991 Kawaguchi
(Continued)

FOREIGN PATENT DOCUMENTS

CN 1198318 A 11/1998
CN 1575153 A 2/2005
(Continued)

OTHER PUBLICATIONS

International Search Report received for PCT Patent Application No. PCT/CN2012/000038, mailed on Mar. 29, 2012, 14 pages (6 pages of English Translation and 8 pages of PCT Search Report).

*Primary Examiner* — Yogesh Patel
(74) *Attorney, Agent, or Firm* — Morrison & Foerster LLP

(57) ABSTRACT

An independent low friction bracket includes a bracket basal body located on a mesh base. The bracket basal body has two side walls, the two side walls and the bracket basal body form a main arch wire slot; upper ends of the two side walls are provided with a ligating wing respectively, and outer surfaces of the two side walls are provided with a slope respectively, so that the side walls each have a gradually reduced wall thickness along the bracket basal body towards the ligating wing, and a recess is disposed at a place where the ligating wing is connected to the side wall.

9 Claims, 2 Drawing Sheets

(56) References Cited

U.S. PATENT DOCUMENTS

| | | | |
|---|---|---|---|
| 5,474,444 A * | 12/1995 | Wildman | 433/8 |
| 6,095,808 A | 8/2000 | Nakagawa | |
| 6,257,882 B1 * | 7/2001 | Wyllie, II | A61C 7/14 433/2 |
| 6,368,108 B1 * | 4/2002 | Locante | A61C 13/0001 433/173 |
| 2005/0244776 A1 | 11/2005 | Abels et al. | |
| 2009/0136891 A1 * | 5/2009 | Song | 433/10 |
| 2010/0003632 A1 * | 1/2010 | Diaz et al. | 433/11 |

FOREIGN PATENT DOCUMENTS

| | | | |
|---|---|---|---|
| CN | 101342094 A | 1/2009 | |
| CN | 102058439 A | 5/2011 | |
| CN | 202051836 U | 11/2011 | |
| EP | 1070484 A2 | 1/2001 | |
| JP | 06233781 A * | 8/1994 | A61C 7/14 |
| WO | 02/064050 A1 | 8/2002 | |
| WO | 03/045266 A1 | 6/2003 | |

\* cited by examiner

INDEPENDENT LOW FRICTION BRACKET

CROSS REFERENCE TO RELATED APPLICATIONS

This application is a U.S. National Phase patent application of PCT/CN2012/000038, filed Jan. 10, 2012, which is hereby incorporated by reference in the present disclosure in its entirety, and which claims priority to Chinese Patent Application No. 201110034375.6, filed Feb. 1, 2011.

FIELD

The present invention relates to the medical device field, and in particularly relates to an independent low friction bracket.

BACKGROUND

According to the clinical ligation manner, orthodontic brackets in current overseas and domestic markets can be classified into a ligating bracket and a self-locking bracket (as for a ligating bracket, a dental arch wire and a bracket are ligated by applying a ligature wire or an elastomeric ring to obtain a tight contact between the dental arch wire and the trench of the bracket, therefore the friction between the dental arch wire and the trench of the bracket is larger; all the conventional brackets belong to the ligating bracket, as shown in the FIG. 1; while as for a self-locking bracket, the dental arch wire does not need to be ligated by the ligature wire, instead of which, an orthodontic dental arch wire is sealed within the trench by applying a slidable or reversible metal cover at an opening towards the lip-cheek of the trench of the bracket, and the orthodontic dental arch wire does not bear any binding force from a lumen formed by the closure cover and the trench, therefore the friction between the orthodontic dental arch wire and the trench of the bracket is smaller, and all the self-locking brackets possess such feature). The self-locking bracket can be further classified into an active self-locking bracket and a passive self-locking bracket. The difference between them is that the closure cover of the passive self-locking bracket is not provided with an elastic design, thus it will not apply any active force to the orthodontic dental arch wire all along. However, the closure cover of the active self-locking bracket has an elastic design, thus the closure cover can apply a force to the orthodontic dental arch wire if the latter reaches a certain size. Most of the self-locking brackets in the current domestic market are imported products or foreign-designed, thus the price is expensive, and the problem that the closure cover usually can not be opened or closed due to an inlay of food residues, deformation under force and the like often occur during the clinical application.

BRIEF SUMMARY

Technical Problems to be Solved

The problems to be solved by the present invention are how to achieve an effect of reducing the friction and how to overcome defects of the self-locking bracket in the prior art that a precise control cannot be performed in later treatment and that the closure cover usually cannot be opened or cannot be closed after being opened due to an inlay of food residues or due to a deformation, without changing the conventional operating manner of clinicians.

Technical Solution

For solving the above technical problems, an independent low friction bracket is provided, which comprises a bracket basal body located on a mesh base, the bracket basal body has two side walls thereon, and the two side walls and the bracket basal body form a main arch wire slot among them; upper ends of the two side walls are provided with a ligating wing respectively; the outer surfaces of the two side walls are provided with a slope respectively, so that the side walls each have a gradually reduced wall thickness in the direction along the bracket basal body towards the ligating wing; a recess is disposed at a place where the ligating wing is connected to the side wall.

Preferably, the upper end of the ligating wing is provided with a tooth position mark.

Preferably, the tooth position mark can be a number, a convex point or a concave point.

Preferably, the recess is an arc-shaped recess.

Preferably, the diameter of the arc-shaped recess is in a range from 0.2 mm to 0.3 mm.

Preferably, the inclination angle of the slope is in a range from 20 degrees to 60 degrees.

Preferably, the independent low friction bracket further includes a fine arch wire located in the main arch wire slot, and the diameter $\Phi$ of the fine arch wire is less than or equal to 0.016".

Preferably, the independent low friction bracket further includes a thick arch wire located in the main arch wire slot, and the diameter $\Phi$ of the thick arch wire is greater than or equal to 0.017".

Preferably, the independent low friction bracket further includes a square wire located in the main arch wire slot, and the sectional size of the square wire is 0.017"×0.025".

Preferably, the mesh base is a metal mesh base.

Beneficial Effect

By improving the existing common bracket, the present invention realizes the effect of reducing the friction and overcomes defects of the self-locking bracket in the prior art that a precise control cannot be performed in later treatment and that the closure cover usually cannot be opened or cannot be closed after being opened due to an inlay of food residues or due to a deformation, without changing the conventional operating manner of clinicians.

Figure 1:
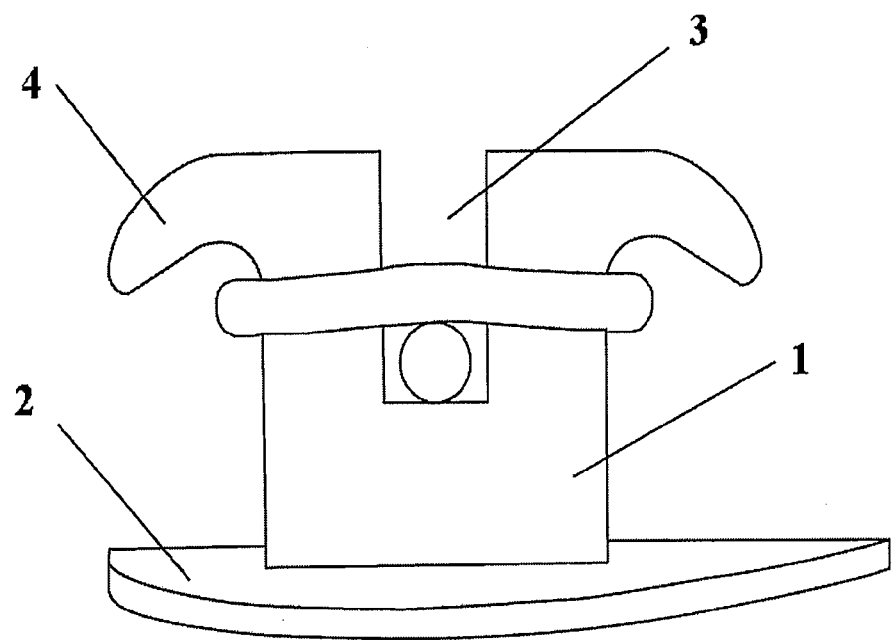
FIG. 1 is a schematic view of an existing common bracket in the active ligation status.

In the drawings, 1: bracket basal body; 1-1, 1-2: side walls; 1-2a: outer surface of side wall 1-2; 1-1b and 1-2b: upper end of each side wall; 2: mesh base; 3: main arch wire slot; 4: ligating wing; 5-1: slope; 5-2: arc-shaped recess; 6: tooth position mark; 8: ligature wire or ligature ring; 9: arch wire; and 10: square wire.

DETAILED DESCRIPTION

Hereinafter, the embodiments of the present invention will be described in further details in combination with the drawings and embodiments. The embodiments below are used for describing the present invention, but not for limiting the scope thereof.

Figure 2:
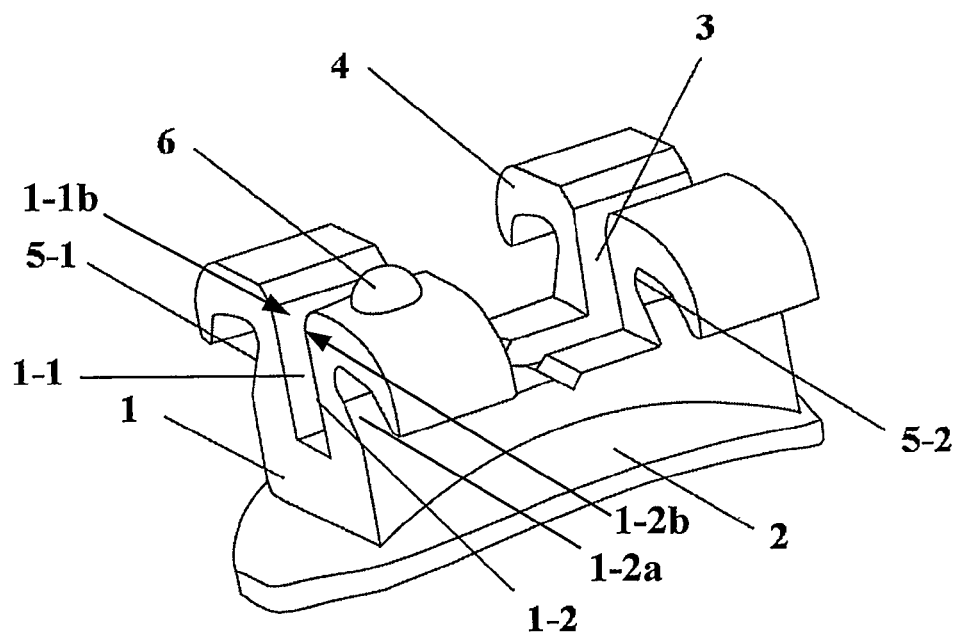
FIG. 2 is a structural schematic view of an independent low friction bracket according to one embodiment of the present invention.

As shown in FIG. 2, the present disclosure provides an independent low friction bracket. The independent low friction bracket comprises bracket basal body 1, mesh base 2, main arch wire slot 3, ligating wing 4, slope 5-1 for introducing ligation, and arc-shaped recess 5. Bracket basal body 1 is located on mesh base 2. Bracket basal body 1 has side walls 1-1 and 1-2 thereon. Side walls 1-1 and 1-2 and bracket basal body 1 form main arch wire slot 3. Upper ends 1-1b and 1-2b of side walls 1-1 and 1-2, respectively, are provided with ligating wing. The outer surfaces of the two side walls (e.g., outer surface 1-2a as seen in FIG. 2) are provided with slope 5-1 for introducing ligation and arc-shaped recess 5-2 respectively. Slope 5-1 is configured to have a gradually reduced wall thickness in the direction along bracket basal body 1 towards ligating wing 4. Compared with the common bracket in the prior art, the present embodiment modifies the vertical outer surface of the side wall of the common bracket into slope 5-1 for introducing ligation and arc-shaped recess 5-2 located at the bottom of the slope. The upper end of the ligating wing 4 is provided with tooth position mark 6. Tooth position mark 6 is used for distinguishing the positions at the bracket facing the gingival and the jaw. Tooth position mark 6 can be a number, a convex point or a concave point. A longitudinal axis is located in the middle of the side wall to act as a reference when the bracket is clinically bonded. The diameter of the arc-shaped recess is in a range from 0.2 mm to 0.3 mm. The inclination angle of slope 5-1 is in a range from 20 degrees to 60 degrees.

Figure 3:
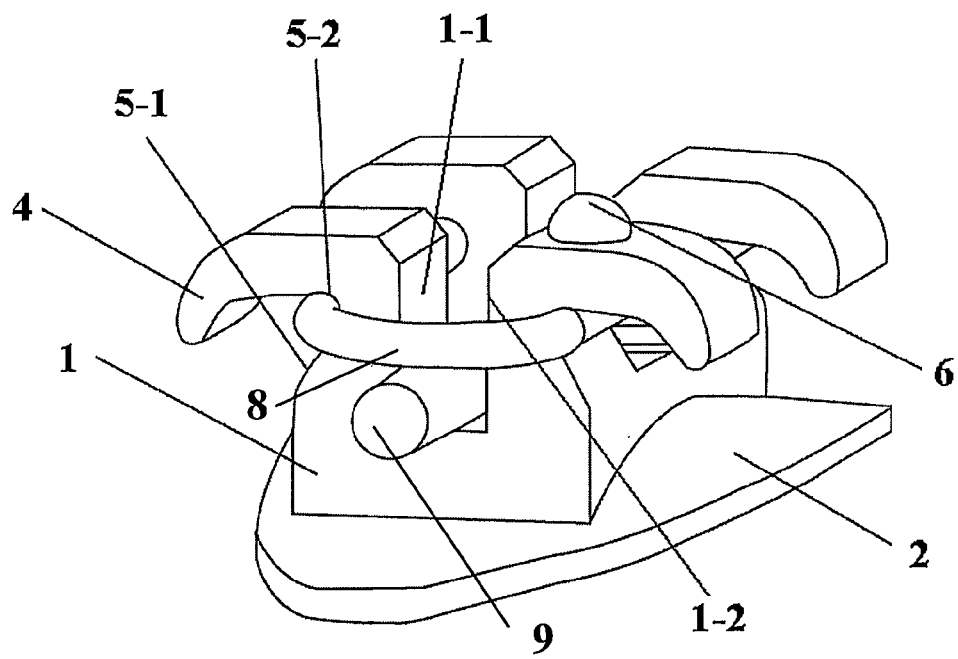
FIG. 3 is a structural schematic view of an independent low friction bracket in a passive ligation status during an early stage according to one embodiment of the present invention.

The independent low friction bracket of the present embodiment is bonded to the dental face in the same bonding manner as that of the common bracket. After the binder is solidified, a fine arch wire or a nickel-titanium round wire has a diameter $\Phi$ less than or equal to 0.016" is placed into the main arch wire slot 3, and ligation is done in a conventional method. As shown in FIG. 3, due to the design of slope 5-1 for introducing ligation, it is hard for ligature wire or ligature ring 8 to be fixed on the middle of the slope, and ligature wire/ligature ring 8 can only slide into arc-shaped recess 5-2 at the bottom of the slope along the slope and fixed thereto. Therefore, there is no binding force between ligature wire/ligature ring 8 and main arch wire 9, so that a passive ligated status is obtained. As a result, teeth can move quickly, and those functions of a common self-locking bracket can be totally reached.

Figure 4:
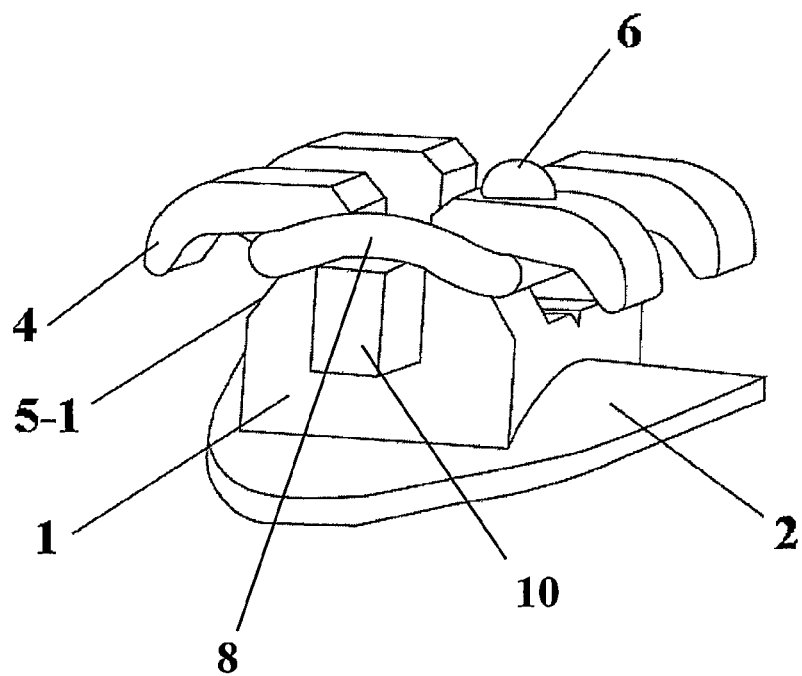
FIG. 4 is a structural schematic view of an independent low friction bracket in an active ligation status during a later stage according to one embodiment of the present invention.

In the later stage of the treatment, clinically, the teeth need to be controlled precisely. As for the independent low friction bracket of the present embodiment, it only needs to replace the main arch wire with one of a diameter greater than or equal to 0.017" or with a standard square wire of a sectional size large than 0.017"×0.025", and the ligation can be done in a conventional method. Now a tight binding is produced between the ligature wire and the main arch wire. As shown in FIG. 4, under an active ligating status, the clinician can adjust and control the teeth precisely.

Compared with all kinds of self-locking brackets for current clinical use, the design of the present invention further possesses better controllability. A clinician has no need to consider when and how to proceed ligation, but only adopt the routine ligation method, and the friction is changed automatically from small to large with the change of the orthodontic arch wire from fine to thick. The bracket not only maintains the conventional operating manner of clinicians, but also solves the problem that the it's hard for the passive self-locking bracket to control teeth precisely in the later stage of an orthodontic treatment, and overcomes the defects that the closure cover can not be opened or closed after being opened due to an inlay of food residues or due to a deformation under force. Therefore the promotion and application thereof are of very considerable prospects.

The independent low friction bracket neither changes the conventional operating manner of orthodontic clinicians, nor adds other auxiliary tools to operate with. An effect from a passive ligation with low friction to an active ligation with conventional friction can be realized as long as the fine orthodontic arch wire is replaced with the thick one continuously with the proceeding of the orthodontic treatment. Under the passive ligated status, there is no binding force between the ligature wire and the orthodontic arch wire, therefore teeth can move quickly to reach an effect of reducing the friction by self-locking bracket; while under the active ligating status, there is a tight binding between the ligature wire or the ligature ring and the main arch wire, therefore the teeth can be torque-controlled and adjusted precisely.

Compared with all kinds of self-locking brackets for current clinical use, the independent low friction bracket designed in the present invention possesses better controllability. It not only maintains the conventional operating manner of clinicians, but also solves the problem that it's hard for the passive self-locking bracket to control teeth precisely in the later stage of the treatment, and overcomes the defects that the closure cover can not be opened or closed after being opened due to an inlay of food residues or due to a deformation under force, and hence possesses good market prospect and extremely high promotion value.

The above are only preferred embodiments of the present invention, it should be pointed out that many modifications and variations can be made thereto for a person skilled in the art without departing from the technical principle of the present invention, those modifications and variations should also be regarded as falling within the scope thereof.

INDUSTRIAL APPLICABILITY

It can be seen from the above embodiments that, the independent low friction bracket provided by the present embodiment possesses better controllability. It not only maintains the conventional operating manner of clinicians, but also solves the problem that it's hard for the passive self-locking bracket to control teeth precisely in the later stage of the treatment, and overcomes the defect that the closure cover can not be opened or closed after being opened due to an inlay of food residues or due to a deformation under force, and hence possesses good market prospect and extremely high promotion value.

What is claimed is:
1. An orthodontic system comprising:
   a mesh base,
   a bracket basal body,
   an arch wire, and
   a ligature wire or ligature ring,
   wherein the bracket basal body is located on the mesh base,
   wherein the bracket basal body has two side walls, and each of the two side walls has an inner surface, an outer surface, and an upper end, wherein the inner surfaces of the two side walls form an arch wire slot, and wherein the arch wire is located in the arch wire slot, wherein a portion of each side wall has a gradually reduced wall thickness in the direction towards the upper end of the corresponding side wall to form a slope on the outer surface of the corresponding side wall, and each slope has an inclination angle in a range from 20 degrees to 60 degrees relative to the mesh base in the mesiodistal direction, wherein the upper end of each side wall is independently connected to at least one ligating wing, and a recess is present where each of the ligating wing is connected to the upper end of the corresponding side wall, wherein the ligature wire or ligature ring is in contact with each recess of each of the ligating wing, and wherein the ligature wire or ligature ring passively engaged with the arch wire when the orthodontic system is clinically bonded to a subject.

2. The orthodontic system of claim 1, wherein an upper end of one of the ligating wings has a tooth position mark.

3. The orthodontic system of claim 2, wherein the tooth position mark is a number, a convex point or a concave point.

4. The orthodontic system of claim 1, wherein each recess is an arc-shaped recess.

5. The orthodontic system of claim 4, wherein each arc-shaped recess has a diameter in a range from 0.2 mm to 0.3 mm.

6. The orthodontic system of claim 1, wherein the arch wire has a diameter $\Phi$ less than or equal to 0.016".

7. The orthodontic system of claim 1, wherein the arch wire has a diameter $\Phi$ greater than or equal to 0.017".

8. The orthodontic system of claim 1, wherein the arch wire is a square wire having a sectional size of 0.017"×0.025".

9. The orthodontic system of claim 1, wherein the mesh base is a metal mesh base.

* * * * *